United States Patent [19]

Welstead, Jr.

[11] Patent Number: 4,624,961
[45] Date of Patent: Nov. 25, 1986

[54] METHOD FOR ENHANCING MEMORY OR CORRECTING MEMORY DEFICIENCY WITH ARYLAMIDOPYRAZOLIDINES AND ARYLAMIDODIAZABICYCLOALKANES

[75] Inventor: William J. Welstead, Jr., Richmond, Va.

[73] Assignee: A. H. Robins Company, Incorporated, Richmond, Va.

[21] Appl. No.: 724,324

[22] Filed: Apr. 17, 1985

[51] Int. Cl.$^4$ .......................................... A61K 31/415
[52] U.S. Cl. .................................................. 514/403
[58] Field of Search ............................... 514/403, 404

[56] References Cited

U.S. PATENT DOCUMENTS 4,207,327  6/1980  Lunsford et al. .................. 514/404

Primary Examiner—Stanley J. Friedman

[57] ABSTRACT

A pharmaceutical method for improving memory or correcting memory deficiency is disclosed, utilizing compounds having the formula:

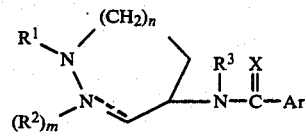

wherein m and n are zero and one and when m is zero, the dotted line represents a double bond; X is oxygen or sulfur; $R^1$ and $R^2$ are hydrogen, loweralkyl, phenyl or phenylloweralkyl, or $R^1$ and $R^2$ taken together may form a fused second ring with the nitrogen atoms having three or four methylene groups to which may be attached at any second ring carbon atom thereof, a loweralkyl or phenyl radical; $R^3$ is hydrogen or loweralkyl; Ar is phenyl, pyridyl, furanyl, thienyl, methoxy-1H-benzotriazolyl, indolinyl, methoxyindolinyl, methoxypyrimidinyl, aminomethoxypyrimidinyl, 1,3-benzodioxolyl or naphthalenyl, the active optical isomers; and the pharmaceutically acceptable acid addition salts thereof.

22 Claims, No Drawings

METHOD FOR ENHANCING MEMORY OR CORRECTING MEMORY DEFICIENCY WITH ARYLAMIDOPYRAZOLIDINES AND ARYLAMIDODIAZABICYCLOALKANES

BACKGROUND OF THE INVENTION

1. Field of Invention

This invention relates to a method of improving the memory of living animals with certain arylamidopyrazolidines and arylamidodiazabicycloalkanes. The invention contemplates the treatment of memory deficiencies and disorders associated with Alzheimers disease and other forms of senility.

2. Information Disclosure Statement

Various chemicals such as physostigmine, arecholine, choline, or piracetam have been reported to facilitate memory in animals, KIRK OTHMER, ENCYCL. CHEM. TECHNOL., 3rd Ed. (1981) Vol. 15, pp 132–142 and ANNUAL REPORTS IN MEDICINAL CHEMISTRY (1984) Vol. 19, pp 31–43. The cardiovascular drug procainamide has been tested for learning enhancement activity in experimental animals of different ages and has been said to improve learning deficits in aging rats KIRK-OTHMER ibid p. 139. Ergoloid Mesylates have been used in treatment of impaired mental function in the elderly. The ergoloid mesylates may in some cases give rise to nausea during treatment for mental impairment and may possess $\alpha$-adrenergic blocking activity. THE MERCK INDEX 10th Ed. 3596 and PHYSICIANS 'DESK REF., 38th Ed. 1984, pp 911–912. In contrast, certain of the compounds of the formula used in the present invention have antinauseant properties and are not $\alpha$-adrenergic blocking agents, cholinomimetics, cholinesterase inhibitors or stimulants.

N-(4-Pyrazolidinyl)benzamides encompassed by Formula I and useful in the method of this invention are disclosed as having anti-emetic and gastric emptying properties and are claimed in U.S. Pat. No. 4,207,327.

N-(1-Substituted-4,5-dihydro-1H-pyrazol-4-yl)benzamides encompassed by Formula I wherein the dotted line is a double bond and useful in the method of this invention are disclosed in U.S. application Ser. No. 597,421 filed on April 6, 1984, as having gastrokinetic and anti-emetic activity.

Benzamido and phenylcarbamoyl diazabicycloalkane derivatives useful in the method of the present invention are disclosed as useful in controlling gastric intestinal motility and as anti-emetics in U. K. patent application GB No. 2,105,707A hereby incorporated by reference. Such compounds are exemplified by 4-amino-5-chloro-2-methoxy-N-(3-[1,6-diazabicyclo[4,4,0]decyl])benzamide and 4-amino-5-chloro-2-methoxy-N-(3-[1,5-diazabicyclo[4,3,0]none-7-enyl]) benzamide.

SUMMARY OF THE INVENTION

The arylamidopyrazolidines and arylamidodiazabicycloalkanes useful in the method of this invention for improving memory or correcting memory deficiency have the general formula:

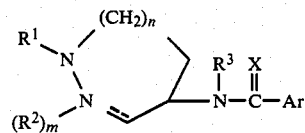

Formula I wherein m and n are zero or one and when m is zero, the dotted line represents a double bond; X is oxygen or sulfur; $R^1$ and $R^2$ are hydrogen, loweralkyl, phenyl and phenylloweralkyl, alkyl, or $R^1$ and $R^2$ may fuse to form a second ring, together with the two nitrogen atoms, having three or four methylene groups optionally substituted by loweralkyl or phenyl radicals; $R^3$ is hydrogen or loweralkyl; Ar is selected from

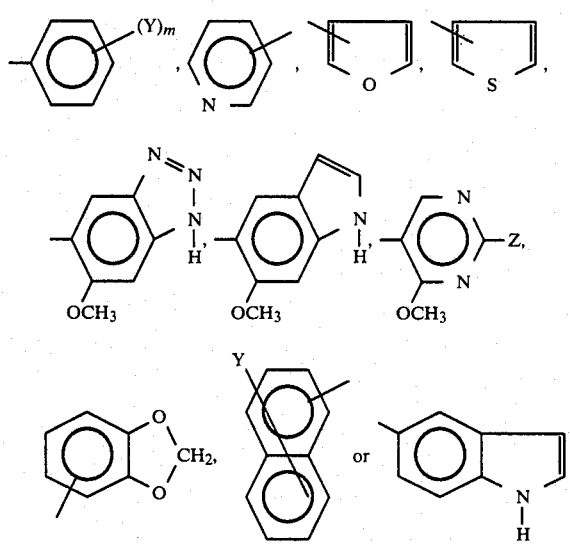

Y is hydrogen loweralkoxy, loweralkylthio, halo, trifluoromethyl, amino, loweralkylamino, diloweralkylamino, acylamino, acyl, aminosulfonyl, loweralkylsulfonyl, nitro, or aminocarbonyl; m is one to three inclusive; Z is amino, lower-alkylamino or diloweralkylamino; the active optical isomers; and the pharmaceutically acceptable acid addition salts which include hydrates and alcoholates thereof.

The compounds are administered for their memory enhancing effect, using usual pharmaceutical procedures and carriers as described hereinbelow.

In the further definition of symbols and in the formulas hereof and where they appear elsewhere throughout this specification and in the claims, the terms have the following significance.

The term "loweralkyl" as used herein, unless otherwise specified, includes straight and branched chain radicals of up to eight carbons inclusive and is exemplified by such groups as methyl, ethyl, propyl, isopropyl, butyl, sec-butyl, tert-butyl, amyl, isoamyl, hexyl, heptyl and octyl radicals and the like. The term "loweralkoxy" has the formula -O-loweralkyl.

The term "halo" or "halogen" when referred to herein includes fluorine, chlorine, bromine and iodine unless otherwise stated.

"Pharmaceutically acceptable salts" include acid addition salts and hydrates and alcoholates thereof which are physiologically compatible in living animals. The acid addition salts may be formed by either strong or weak acids. Representative of strong acids are hydrochloric, hydrobromic, sulfuric and phosphoric acids. Representative of weak acids are fumaric, maleic, mandalic, tartaric, citric, oxalic, succinic, hexamic and the like.

The test relied upon to test for memory enhancement involves a passive avoidance procedure with trained mice as described hereinbelow under "Pharmacological Testing."

Synthesis methods used to prepare compounds of Formula I are illustrated by equation in Chart I.

Methods of preparation of starting amino compounds of Formula II (See Chart I) are given in U.S. Pat. No. 4,207,327 and GB No. 2,105,707A.

CHART I

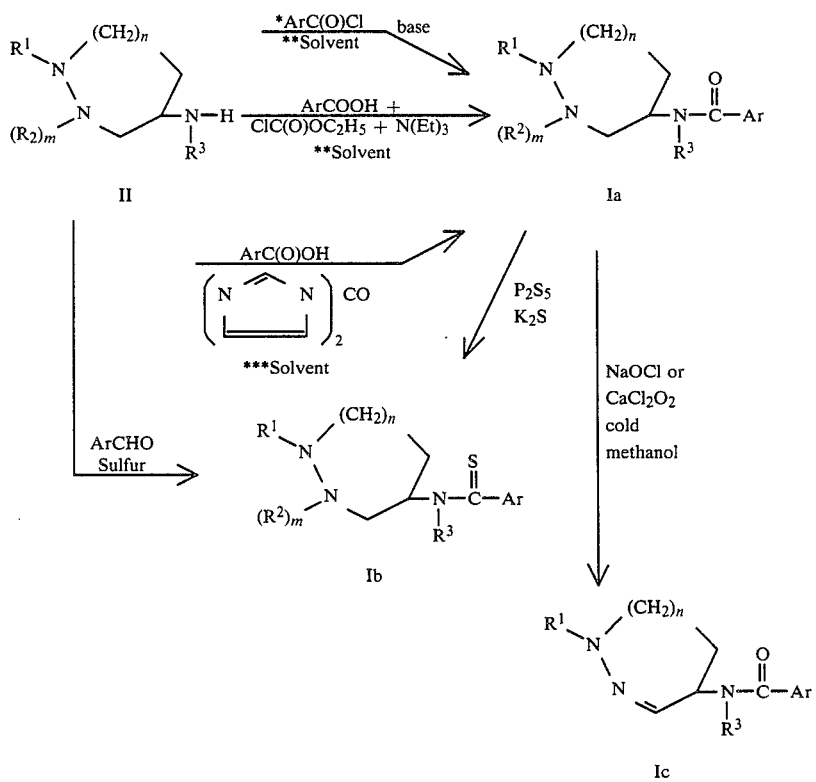

Footnotes:
Symbols are as defined under Formula I except in the case of *ArC(O)Cl which cannot have unprotected amine substitution.
**Suitable solvents are methylene chloride, chloroform, and diethyl ether.
***Suitable solvent is tetrahydrofuran.

A preferred group of compounds encompassed by Formula I useful in the method of this invention have the formula:

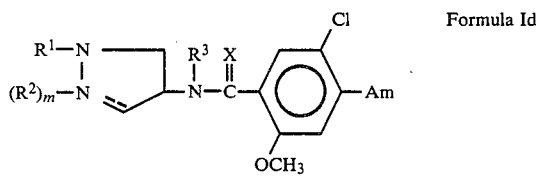

Formula Id wherein:
$R^1$ and $R^2$ are selected from hydrogen, loweralkyl, phenyl or phenylloweralkyl;
m is zero or one and when m is zero, the dotted line represents a double bond;
$R^3$ is hydrogen or loweralkyl;
X is oxygen or sulfur;
Am is amino (i.e., —NH$_2$) or loweralkylamino; the active optical isomers; and the pharmaceutically acceptable acid addition salts thereof.

The following examples are provided merely by way of illustrating the methods of preparation of compounds useful in the method of the invention and are not to be construed as limiting in nature.

EXAMPLE 1

4-Fluoro-N-(1,2-diethyl-4-pyrazolidinyl)benzamide

The title compound was prepared as described in Example 2 of U.S. Pat. No. 4,207,327 from 1,2-diethyl-4-phthalimidopyrazolidine maleate and p-fluorobenzoyl chloride, m.p. 114°–116° C.

EXAMPLE 2

4-Nitro-N-(1,2-diethyl-4-pyrazolidinyl)benzamide Hydrochloride

The title compound was prepared as described in Example 4 of U.S. Pat. No. 4,207,327 from 4-amino-1,2-diethylpyrazolidine and p-nitrobenzoyl chloride.

EXAMPLE 3

4-Amino-N-(1,2-diethyl-4-pyrazolidinyl)benzamide

The title compound was prepared as described in Example 5 of U.S. Pat. No. 4,207,327 by catalytic hydrogenation of 4-nitro-(1,2-diethyl-4-pyrazolidinyl)benzamide, m.p. 119°–121° C.

EXAMPLE 4

4-Amino-5-chloro-2-methoxy-N-(1.2-diethyl-4-pyrazolidinyl)benzamide

The title compound was prepared as described in Example 6 of U.S. Pat. No. 4,207,327 from 4-acetamido- 5-chloro-2-methoxy-benzoic acid thionyl chloride and 4-amino-1,2-diethylpyrazolidine, m.p. 117°–119° C.

EXAMPLE 5

3,4,5-Trimethoxy-N-(1,2-dimethyl-4-pyrazolidinyl)benzamide

The title compound was prepared as described in Example 3 of U.S. Pat. No. 4,207,327 from 4-amino-1,2-dimethylpyrazolidine and 3,4,5-trimethoxybenzoyl chloride, m.p. 163°–166° C.

EXAMPLE 6

4-Acetylamino-N-(1,2-diethyl-3-pyrazolidinyl)benzamide

To 6 g (0.022 mole) of p-amino-N-(1,2-diethyl-4-pyrazolidinyl)benzamide and 2.2 g (0.022 mole) of triethyl amine in 50 ml of methylene chloride was added dropwise 2.5 g (0.025 mole) of acetic anhydride. The mixture was stirred overnight and partitioned between dilute potassium carbonate and chloroform. The organic layer was dried over anhydrous sodium sulfate and concentrated. The residue was crystallized twice from ethyl acetate to give 4.4 g (66%) of title compound, m.p. 178°–180° C.

Analysis: Calculated for $C_{16}H_{24}N_4O_2$: C,63.13; H, 7.94; N, 18.41; Found: C, 63.05; H,7.92; N, 18.44.

EXAMPLE 7

4-Amino-5-chloro-2-methoxy-N-(1,2-dimethyl-4-pyrazolidinyl)benzamide

The title compound was prepared as described in Example 8 of U.S. Pat. No. 4,207,327 from 4-amino-5-chloro-2-methoxybenzoic acid, triethylamine, ethylchlorocarbonate and 4-amino-1,2-dimethylpyrazolidine, m.p. 169°–171° C.

EXAMPLE 8

4-Amino-5-chloro-2-methoxy-N-(1-isopropyl-2-methyl-4-pyrazolidinyl)benzamide Dihydrochloride The title compound was prepared as described in Example 11 of U.S. Pat. No. 4,207,327 from 4-amino-5-chloro-2-methoxybenzoic acid, ethylchlorocarbonate and 4-amino-1-isopropyl-2-methylpyrazolidine and hydrogen chloride, m.p. 182°–186° C.

EXAMPLE 9

4-Amino-5-chloro-2-methoxy-N-(1-benzyl-2-methyl-4-pyrazolidinyl)benzamide Fumarate The title compound was prepared as described in Example 9 of U.S. Pat. No. 4,207,327 from 4-amino-5-chloro-2-methoxybenzoic acid, ethylchlorocarbonate, 4-amino-1-benzyl-2-methyl-pyrazolidine and fumaric acid, m.p. 129°–131° C.

EXAMPLE 10

4-Amino-5-chloro-2-methoxy-N-(1-cyclohexyl-2-methyl-4-pyrazolidinyl)benzamide, Hydrochloride,Hydrate [1:1:1]

The title compound was prepared as described in Example 10 of U.S. Pat. No. 4,207,327 from 4-amino-5-chloro-2-methoxybenzoic acid, ethylchlorocarbonate and 4-amino-1-cyclohexyl-2-methylpyrazolidine, m.p. 105°–120° C.

EXAMPLE 11

4-Amino-5-chloro-2-methoxy-N-[1,2-bis(1-methylethyl)-4-pyrazolidinyl]benzamide, Hydrochloride, Hydrate [1:1:1]

A sample of 7 g (0.17 mole) of 1,2-bis(1-methylethyl)-4-pyrazolidineamine difumarate hemihydrate was partitioned between methylene chloride and dilute sodium hydroxide. The organic layer was dried with anhydrous sodium sulfate and stirred 18 hr with Type 4A molecular sieves and filtered.

In another flask 1.9 g (0.017 mole) of ethyl chloroformate in methylene chloride was added dropwise to a suspension of 3.5 g (0.017 mole) of 4-amino-4-chloro-2-methoxybenzoic acid and 1.7 g 0.017 mole) of triethylamine in methylene chloride at −10° C. The resulting solution was stirred 30 minutes at −10° C. and the aminopyrazolidine (prepared above) was added dropwise at −10° C. The temperature was allowed to rise to 20° C. over a period of 1.5 hr. The solution was extracted with saturated sodium bicarbonate, dried over anhydrous sodium sulfate and concentrated. The residue was partitioned between ethyl acetate and dilute hydrochloric acid. The acid layer was made basic with dilute sodium hydroxide and extracted with chloroform. The chloroform layer was dried (anhydrous sodium sulfate) and concentrated. The residue was dissolved in isopropyl alcohol and made acidic with ethereal hydrogen chloride. The resulting crystals were collected. Yield of title compound was 1.3 g (19%), m.p. 160°–164° C.

Analysis: Calculated for $C_{17}H_{30}N_4O_3Cl_2$: C, 49,88; H,7.39; N,13.69; Found: C,49.83; H,7.15; N,13.57.

EXAMPLE 12

4-Amino-5-chloro-N-(1-ethyl-4,5-dihydro-1H-pyrazol-4-yl)-2-methoxybenzamide

To a solution of 8.90 g (0.020 mole) of 4-amino-5-chloro-N-(1,2-diethyl-4-pyrazolidinyl)-2-methoxybenzamide succinate in 400 ml of reagent grade methanol, cooled to −20° C. and under nitrogen atmosphere was added dropwise 80 ml of 5% aqueous sodium hypochlorite over a 20 min period while maintaining the reaction mixture at −20° C. The reaction mixture was stirred for an additional one hour period at 0° C. then diluted with one liter of chloroform. The diluted mixture was washed with 500 ml of water. The aqueous layer was extracted with 200 ml of chloroform. The combined chloroform layers were dried over sodium sulfate and concentrated in vacuo. The crude product was partially purified by column chromatography on a silica column (eluted with ethyl acetate:hexane:methanol, 4.5:4.5:1). Further purification was effected by high pressure liquid chromatography, using the same solvent system as eluant. On evaporation, the residue was triturated with cold diethyl ether to give 1.90 g (32.0%) of title product, m.p. 132.5°–134.0° C.

Analysis: Calculated for $C_{13}H_{17}N_4O_2Cl$: C, 52.61; H, 5.78; N, 18.87; Found: C, 51.98; H, 5.81; N, 18.40.

EXAMPLE 13

4-Amino-5-chloro-N-(4,5-dihydro-1-methyl-1H-pyrazol-4-yl)-2-methoxybenzamide

To a solution of 1.44 g (0.00482 mole) of 4-amino-5-chloro-2-methoxy-N-(1,2-dimethyl-4-pyrazolidinyl benzamide in 100 ml of methanol, cooled to −30° C. and under nitrogen atmosphere was added dropwise 10.5 ml (0.007 mole) of 5% aqueous sodium hypochlorite over a 15 minute period. The mixture was slowly warmed to 0° C. at which temperature it was stirred for 1 hr. The mixture was diluted with 250 ml of chloroform and extracted successively with 100 ml of water and 100 ml of saturated sodium chloride solution. The chloroform layer was dried over sodium sulfate and concentrated in vacuo. The concentrate was filtered through silica gel (eluted with ethyl acetate: hexane:methanol, 4.5:4.5:1). The filtrate was concentrated and the residue was triturated with cold diethyl ether to give 0.58 g (43%) of the title product as white powder, m.p. 173°–175° C.

Analysis: Calculated for $C_{12}H_{15}N_4O_2Cl$: C, 50.97; H, 5.35; N, 19.82; Found: C, 50.82; H, 5.39; N, 19.58.

EXAMPLE 14

N-(4,5-Dihydro-1-ethyl-1H-pyrazol-4-yl)4-fluorobenzamide

In accordance with the procedure of Example 12, N-(1,2-diethyl-4-pyrazolidinyl)-4-fluorobenzamide is reacted with sodium hypochlorite and the product is isolated.

EXAMPLE 15

N-(4,5-Dihydro-1-ethyl-1H-pyrazol-4-yl)-3,4,5-trimethoxybenzamide

In accordance with the procedure of Example 12, N-(1,2-dimethyl-4-pyrazolidinyl)-3,4,5-trimethoxybenzamide is reacted with sodium hypochlorite and the product is isolated.

EXAMPLE 16

N-(4,5-dihydro-1-ethyl-1H-pvrazol-4-yl)4-nitrobenzamide

In accordance with the procedure of Example 12, N-(1,2-diethyl-4-pyrazolidinyl)-4-nitrobenzamide is reacted with sodium hypochlorite and the product is isolated.

EXAMPLE 17

4-Amino-N-(4,5-dihydro-1-ethyl-1H-pyrazol-4-yl) benzamide

In accordance with the procedure of Example 12, 4-amino-N-(1,2-diethyl-4-pyrazolidinyl)benzamide is reacted with sodium hypochlorite and the product is isolated.

EXAMPLE 18

When in accordance with the procedure of Example 12, the following are reacted with sodium hypochlorite:
N-(1,2-dimethyl-4-pyrazolidinyl)-4-cyanobenzamide,
N-(1,2-dimethyl-4-pyrazolidinyl)-3-trifluorobenzamide,
N-(1,2-dimethyl-4-pyrazolidinyl-4-methylbenzamide,
N-(1,2-dimethyl-4-pyrazolidinyl-4-methoxybenzamide,
4-acetamido-N-(1,2-dimethyl-4-pyrazolidinyl)benzamide,
N-(1,2-dimethyl-4-pyrazolidinyl-2-methoxy-5-sulfamoylbenzamide, and
(1,2-dimethyl-4-pyrazolidinyl-4-hydroxybenzamide,
there are obtained:
N-(4,5-dihydro-1-methyl-1H-pyrazol-4-yl)-4-cyanobenzamide,
N-(4,5-dihydro-1-methyl-1H-pyrazol-4-yl)-3-trifluoromethylbenzamide,
N-(4,5-dihydro-1-methyl-1H-pyrazol-4-yl)-4-methylbenzamide,
N-(4,5-dihydro-1-methyl-1H-pyrazol-4-yl)-4-methoxybenzamide,
4-acetamide-N-(4,5-dihydro-1-methyl-1H-pyrazol-4-yl)benzamide,
N-(4,5-dihydro-1-methyl-1H-pyrazol-4-yl)-2-methoxy5-sulfamoyl)benzamide, and
N-(4,5-dihydro-1-methyl-1H-pyrazol-4-yl)-4-hydroxybenzamide.

EXAMPLE 19

N-(4,5-dihydro-1-ethyl-1H-pyrazol-4-yl)-4-(methylamino)-5-chloro-2-methoxybenzamide In accordance with the procedure of Example 12, 5chloro-2-methoxy-4-(methylamino)-N-(1,2-diethyl-4-pyrazolidinyl)benzamide is reacted with sodium hypochlorite and the product is isolated.

EXAMPLE 20

N-(4,5-dihydro-1-ethyl-1H-pyrazol-4-yl)-5-chloro-4-(dimethylamino)-2-methoxybenzamide In accordance with the procedure of Example 12, 5-chloro-4-(dimethylamino)-2-methoxy-N-(1,2-diethyl-4-pyrazolidinyl) benzamide is reacted with sodium hypochlorite and the product is isolated.

EXAMPLE 21

5-Bromo-N-(1,2-diethyl-4-pyrazolidinyl)-2,4-dimethoxybenzamide Hemihydrate

A solution of triethylamine (1.52 g, 0.0150 mole) in 5 ml methylene chloride was added to a stirred solution of 5-bromo-2,4-dimethoxybenzoic acid (3.92 g, 0.0150 mole) in 75 ml of methylene chloride. After stirring for 20 minutes at room temperature, the mixture was cooled to 0° C. with an ice water bath. A solution of ethyl chloroformate (1.63 g, 0.0150 mole) in 10 ml methylene chloride was added dropwise to the cold stirred reaction mixture, and the mixture stirred at 0° C. for 30 minutes. Then a solution of 4-amino-1,2-diethylpyrazolidine (2.15 g, 0.0150 mole) in 10 ml of methylene chloride was added dropwise to the cold reaction mixture. The mixture was stirred for 30 minutes at 0° C. and then allowed to warm to room temperature and stirred for 16 hr. The mixture was concentrated to a semi-solid residue which was triturated in 10 ml methanol and 20 ml of a saturated aqueous sodium bicarbonate solution. The mixture was extracted with 2×75 ml portions of methylene chloride, the extract dried (magnesium sulfate) and concentrated to give a solid. The solid was triturated with isopropyl ether and filtered to give 4.28 g (73.9%) of cream-colored solid; recrystallization from isopropyl ether gave 2.04 g of the product; m.p. 113.5°–114.5° C. NMR analysis showed the solid to be a monohydrate, vacuum drying at 54° C. for 16 hrs gave the hemihydrate, m.p. 114°–115° C.

Analysis: Calculated for $C_{16}H_{24}N_3O_3BrO.5H_2O$: C, 48.62; H, 6.37; N, 10.63; Found: C, 48.75; H, 6.12; N, 10.61.

EXAMPLE 22

N-(1,2-Diethyl-4-pyrazolidinyl)-2,4-dimethoxybenzamide, Monohydrochloride

A solution of 4-amino-1,2-diethylpyrazolidine (1.83 g, 0.0128 mole) in 20 ml ether was added dropwise to a stirred solution of 2,4-dimethoxybenzoyl chloride (2.56 g, 0.0128 mole) in 100 ml ether. The mixture was stirred at ambient temperature for 18 hrs, and the solid was collected under nitrogen. Because of an impurity, the free base of the product was generated to give 1.80 g (46%) of a clear oil. The oil was dissolved in 20 ml absolute ether, and treated with 0.49 ml concentrated hydrochloric acid. This mixture was diluted with isopropyl ether to precipitate 1.60 g of the hydrochloride salt, which was filtered off and dried in vacuo for 16 hrs; m.p. 150°–152° C.

Analysis: Calculated for $C_{18}H_{26}N_3O_3Cl$: C, 55.89; H, 7.62; N,12.22; Found: C, 55.81; H, 7.74; N, 12.18.

EXAMPLE 23

N-(1.2-Diethyl-4-pyrazolidinyl)-2-methoxy-5-(methylsulfonyl)-benzamide

Triethylamine (1.01 g, 0.010 mole) was added to a stirred mixture of 5-methylsulfonyl-2-methoxybenzoic acid (2.30 g, 0.010 mole) in 50 ml of methylene chloride. The mixture was cooled to 0° C. for 20 minutes and maintained at this temperature while ethyl chloroformate (1.09 g, 0.010 mole) was added dropwise. After another 20 minutes of stirring at 0° C., a solution of 1,2-diethyl-4-aminopyrazolidine (2.43 g, 0.010 mole) in 10 l of methylene chloride was added dropwise. The reaction mixture was allowed to come to ambient temperature and was stirred for 18 hrs. The reaction mixture was then extracted with 10% sodium bicarbonate solution, the methylene chloride layer separated and dried over magnesium sulfate. The methylene chloride solution was concentrated to give 3.90 g of a tanbrown solid which was recrystallized from water. A sulfate salt was prepared which was converted back to the free base. The solid free base that formed was recrystallized from ethanol-isopropyl ether to give 1.03 g (29%) of title compound; m.p. 123°–124° C. The compound was vacuum dried at 110° C.; the melting point was unchanged.

Analysis: Calculated for $C_{16}H_{25}N_3O_4S$: C, 54.06; H, 7.09; N, 11.82; Found: C,53.88; H, 7.12; N, 11.73.

EXAMPLE 24

N-(1,2-Diethyl-4-pyrazolidinyl)-2-methoxybenzamide

A solution of 2-methoxybenzoyl chloride (3.41 g, 0.020 mole) in 50 ml of toluene was added dropwise to a stirred solution of 1,2-diethyl-4-aminopyrazolidine (2.86 g. 0.020 mole) in 100 ml of toluene. The mixture was stirred at ambient temperature for 2 hrs, and then at reflux temperature for 2 hrs. After standing for 16 hrs, the mixture was extracted with 100 ml of 10% sodium bicarbonate solution. The toluene layer was dried over magnesium sulfate and concentrated to give 4.32 g (81.6%) of oil. The liquid was distilled over magnesium sulfate, b.p. 160° C./0.020 mm Hg, to give 2.52 g of a clear, yellow oil.

Analysis: Calculated for $C_{15}H_{23}N_3O_2$: C, 64.96; H, 8.36; N, 15.15; Found: C, 64.70; H, 8.33; N, 14.89.

EXAMPLE 25

5-Chloro-N-(1,2-diethyl-4-pyrazolidinyl)-2-methoxy-4-methylamino)benzamide

A solution of triethylamine (2.02 g, 0.020 mole) in 10 ml of methylene chloride was added dropwise to a stirred solution of 5-chloro-4-(methylamino)-2-methoxybenzoic acid (4.31 g, 0.020 mole) in 50 ml methylene chloride. The mixture was stirred at 0° C. for 20 minutes, and then a solution of ethyl chloroformate (2.17 g, 0.020 mole) in 10 ml of methylene chloride was added dropwise. This solution was stirred at 20° C. for another 20 minutes. A solution of 4-amino-1,2-diethylpyrazolidine (2.86 g, 0.020 mole) in 10 ml methylene chloride was added dropwise. The reaction mixture was stirred at 0° C. for 30 minutes and then at ambient temperature for 2 hours. Mass spectral analysis of a small sample showed some unreacted acid. The mixture was heated at reflux temperature for 1 hr, and then at ambient temperature for 18 hrs. The reaction mixture was extracted with 50 ml of a 2N sodium hydroxide solution. The methylene chloride layer was separated, dried over magnesium sulfate and concentrated to an oil that crystallized on trituration with isopropyl ether. The product, 4.29 g (63% ) was recrystallized from isooctane (400 ml) to give 3.42 g of white solid; m.p. 99°–101° C. Analysis: Calculated for $C_{16}H_{25}N_4O_2Cl$: C, 56.38; H, 7.39; N, 16.44; Found: C, 56.33; H, 7.39; N, 16.25.

The synthetic preparations of certain compounds encompassed by Formula I and useful in the present invention listed in the following Example 26 a to i are given in British patent application No. 2,105,707A.

EXAMPLE 26 a to i (a) 4-Acetamido-5-chloro-2-methoxy-N-(3-[1,6-diazabicyclo[4.4.0]decyl])benzamide. (See Example 1 of GB No. 2,105,707A).

(b) 4-Amino-5-chloro-2-methoxy-N-(3-[1,6-diazabicyclo[4.4.0]decyl])benzamide. (See Example 2 of GB No. 2,105,707A).

(c) 4-Acetamido-5-chloro-2-methoxy-N-(3-[1,5-diazabicyclo[4.3.0]nona-7-enyl])benzamide. ( See Example 3 of GB No. 2,105,707A).

(d) 4-Amino-5-chloro-2-methoxy-N-(3-[1,5-diazabicyclo [4.3.0]nona-7-enyl])benzamide. (See Example 4 of GB No. 2,105,707A).

(e) 4Amino-5-chloro-2-methoxy-N-(3-[7-phenyl-1,5-diazabicyclo[4.3.0]nonyl])benzamide. (See Example 8 of GB No. 2,105,707A).

(f) 4-Acetamido-5-chloro-2-methoxy-N-(2-[1H-2,3,5,10-tetrahydropyrazolo[1,2-b]phthalazinyl])benzamide. (See Example 9 of GB No. 2,105,707A).

(g) 4-Amino-5-chloro-2-methoxy-N-(2-[1H-2,3,5,10-tetrahydropyrazolo[1,2-b]phthalazinyl])benzamide. See Example 10 of GB No. 2,105,707A).

(h) Three geometric isomers of (±) 4-acetamido-5-chloro-2-methoxy-N-(7-[2-methyl-1,5-diazabicyclo[4.3.0]nonyl]) benzamide, Isomers I, II, and III as identified in Examples 11, 12, and 13 of GB No. 2,105,707A.

(i) Three geometric isomers of (±) 4-amino-5-chloro-2-methoxy-N-(7 or 8)-[2-methyl-1,5-diazabicyclo[4,3,0]) benzamide, Isomers I, II, and III as identified in Examples 14, 15, and 16 of GB No. 2,105,707A.

EXAMPLE 27

4-Amino-5-chloro-2-methoxy-N-(1,2-diethyl-4-pyrazolidinyl)benzamide succinate [1:1]

4-Amino-5-chloro-2-methoxy-N-(1,2-diethyl-4-pyrazolidinyl)benzamide as prepared in Example 6 of U.S. Pat. No. 4,207,327 was added to an isopropyl alcohol solution containing a molecularly equivalent amount of succinic acid. Isopropyl ether was added to precipitate the succinate salt which was then recrystallized from isopropyl ether-isopropyl alcohol mixture. The salt was vacuum dried at 60° C., m.p. 99°–101° C.

Analysis: Calculated for $C_{15}H_{23}N_4O_2Cl \cdot C_4H_6O_4$: C, 51.29; H, 6.57; N, 12.59; Found: C, 51.31; H, 6.64; N, 12.53.

EXAMPLE 28 a to j

Following the procedure of Example 21, each of the following acids are reacted with ethyl chloroformate followed by 4-amino-1,2-diethylpyrazolidine:
picolinic acid,
6-methoxy-1H-benzotriazole-5-carboxylic acid,
indole-6-methoxy-5-carboxylic acid,
2-(dimethylamino)-4-methoxy-5-pyrimidinecarboxylic acid,
4-methoxy-2-(methylamino)-5-pyrimidinecarboxylic acid,
2-amino-4-methoxy-5-pyrimidinecarboxylic acid,
1,-benzodioxole-4-carboxylic acid,
2-furancarboxylic acid,
2-thiophenecarboxylic acid, and
1-naphthoic acid to give the following amides:

(a) N-(1,2-diethyl-4-pyrazolidinyl)-2-pyridinecarboxamide,
(b) N-(1,2-diethyl-4-pyrazolidinyl)-6-methoxy-1H-benzotriazole-5-carboxamide,
(c) N-(1,2-diethyl-4-pyrazolidinyl)-6-methoxy-1H-indole-5-carboxamide,
(d) N-(1,2-diethyl-4-pyrazolidinyl)-2-(dimethylamino)-4-methoxy-5-pyrimidinecarboxamide.
(e) N-(1,2-diethyl-4-pyrazolidinyl)-4-methoxy-2-(methylamino)-5-pyrimidinecarboxamide,
(f) 2-amino-N-(1,2-diethyl-4-pyrazolidinyl)-4-methoxy-5-pyrimidinecarboxamide,
(g) N-(1,2-diethyl-4-pyrazolidinyl)-1,3-benzodioxole-4-carboxamide,
(h) N-(1,2-diethyl-4-pyrazolidinyl)-2-furancarboxamide,
(i) N-(1,2-diethyl-4-pyrazolidinyl)-2-thiophenecarboxamide, and
(j) N-(1,2-diethyl-4-pyrazolidinyl)-1-naphthalenecarboxamide.

Pharmacological Testing (Mice)

The test relied upon to indicate effectiveness of the compounds in the method of this invention as follows involves a passive avoidance procedure which is the type of procedure most often used to evaluate compounds for their effect on memory and learning.

There are three phases to the behavioral procedure: adaptation, training, and testing. Following 24 hrs of water deprivation, the mice are given an adaptation session during which they are allowed to freely explore the chamber and learn the location of the drinking spout. The session is terminated when the animals have completed 5 seconds of drinking. The mice are then given free access to water for 1.5 hrs in their home cages. During the training session, 24 hrs later, the mice are permitted 5 seconds access to the drinking tube after which time the shock circuit is automatically activated and all subsequent contracts with the tube are punished. The training session is terminated when the mice either fail to touch the tube for a 60 second period or receive the maximum number of shocks (5). The latency to complete the initial 5 seconds of drinking, as well as the number of shocks each animal receives is recorded. The animals are then returned to their home cages and given free access to water for the next 24 hrs.

Retention is tested 48 hrs later by once again placing the mice into the lick-suppression chamber and recording the time it takes each animal to complete the 5 seconds of drinking from the water spout. Mice failing to complete the 5 seconds of drinking within 2000 seconds are removed from the apparatus and assigned a maximum test latency score of 2000. Test compound or saline are given 30 minutes prior to the retention task.

As indicated in Table 1, the compound of Example 27; namely, 4-amino-5-chloro-2-methoxy-N-(1,2-diethyl-4-pyrazolidinyl)benzamide succinate, significantly increases the time required to complete the drinking task. This increased latency is a measure of memory improvement in the trained animals.

It should be noted that the increased latency is not due to a general debilitation of the animals, since untrained animals treated with the same doses of the compound of Example 27 do not show a similar delayed latency to drinking.

TABLE 1

Effects on Memory in Mice

| Compound | Dose (mg/kg, i.p.) | Latency to Complete 5 sec. of Drinking ($\bar{X} \pm$ SE) | p |
|---|---|---|---|
| Saline | 0 | 413 ± 69 | — |
| Example 27 | 32 | 443 ± 169 | ns |
| Example 27 | 42 | 439 ± 127 | ns |
| Example 27 | 56 | 800 ± 216 | ns |
| Example 27 | 75 | 874 ± 175 | p < 0.02 |
| Example 27 | 100 | 1264 ± 220 | p < 0.002 |

Pharmaceutical Compositions

The pharmaceutical compositions used in the method of this invention for administration to animals and humans are comprised of, as active ingredients, at least one of the compounds of Formula I, according to the invention, in association with a pharmaceutical carrier or excipient. The compounds are thus presented in a therapeutic composition for oral, parenteral, subcutaneous, intramuscular, intraperitoneal, intravenous, or rectal administration. Thus, for example, compositions for oral administration can take the form of elixirs, capsules, tablets, or coated tablets containing carriers conveniently used in the pharmaceutical art. Suitable tableting excipients include lactose, potato and maize starches, talc, gelatin, stearic and silicic acids, magnesium stearate and polyvinyl pyrrolidones.

For parenteral administration, the carrier or excipient can be comprised of a sterile parenterally acceptable liquid; e.g., water or arachis oil contained in ampoules.

In compositions for rectal administration, the carrier can be comprised of a suppository base; e.g., cocoa butter or a glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount; i.e., such that a suitable effective dosage will be consistent with the dosage form employed in single or multiple unit doses. The exact individual dosages, as well as daily dosages, will of course be determined according to standard medical principles under the direction of a physician or veterinarian. Generally, the pharmacology tests on mice suggest an effective dose for a small animal will be in the range of about 75–100 mg/kg of body weight for a compound such as that of Example 27. Generally, for humans, in the absence of actual testing the amount projected to be required appears to be about 10-100 mg/kg of body weight to produce memory enhancement in humans; for example, in impaired memory of the elderly.

Based on the foregoing projection for effective dosages for humans, daily dosages of about 2 to 4 times the effective dose appear to be reasonable for a total daily dosage range of 20-400 mg/kg of body weight. Obviously, the effective dosage amount may be administered by a variety of unit dosage sizes. The scope of the invention in relation to human dosage is not to be limited by the foregoing projections due to uncertainty in transposing from animal data to human dosages.

What is claimed is:

1. A method of enhancing learning or memory in living animals in need thereof which comprises administering thereto an effective amount for enhancing learning or memory of a compound selected from the group having the formula:

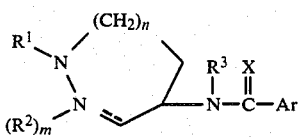

Formula I wherein;
n is zero and m is zero or one and when m is zero, the dotted line represents a double bond;
X is oxygen or sulfur;
$R^1$ and $R^2$ are hydrogen, loweralkyl, phenyl and phenylloweralkyl, or $R^1$ and $R^2$ may fuse to form a second ring, together with the two nitrogen atoms, having three or four methylene groups optically substituted by loweralkyl or phenyl radicals;
$R^3$ is hydrogen or loweralkyl;
Ar is selected from

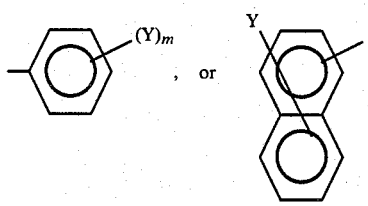

Y is hydrogen, loweralkoxy, loweralkylthio, halo, trifluoromethyl, amino, loweralkylamino, diloweralkylamino, acylamino, acyl, aminosulfonyl, loweralkylsulfonyl, nitro, or aminocarbonyl;
m is one to three inclusive;
the active optical isomers; and the pharaceutically acceptable acid addition salts including hydrates and alcoholates thereof.

2. The method of claim 1 wherein the compound used is 4-fluoro-N-(1,2-diethyl-4-pyrazolidinyl)benzamide or a pharmaceutically acceptable acid addition salt thereof.

3. The method of claim 1 wherein the compound used is 4-nitro-N-(1,2-diethyl-4-pyrazolidinyl)benzamide hydrochloride or a pharmaceutically acceptable acid addition salt thereof.

4. The method of claim 1 wherein the compound used is 4-amino-N-(1,2-diethyl-4-pyrazolidinyl)benzamide or a pharmaceutically acceptable acid addition salt thereof.

5. The method of claim 1 wherein the compound used is 4-amino-5-chloro-2-methoxy-N-(1,2-diethyl-4-pyrazolidinyl) benzamide or a pharmaceutically acceptable acid addition salt thereof.

6. The method of claim 1 wherein the compound used is 4-amino-5-chloro-2-methoxy-N-(1,2-diethyl-4-pyrazolidinyl) benzamide succinate [1:1].

7. The method of claim 1 wherein the compound used is 3,4,5-trimethoxy-N-(1,2-dimethyl-4-pyrazolidinyl)-benzamide or a pharmaceutically acceptable acid addition salt thereof.

8. The method of claim 1 wherein the compound used is 4-acetylamino-N-(1,2-diethyl-3-pyrazolidinyl)benzamide or a pharmaceutically acceptable acid addition salt thereof.

9. The method of claim 1 wherein the compound used is 4-amino-5-chloro-2-methoxy-N-(1,2-dimethyl-4-pyrazolidinyl) benzamide or a pharmaceutically acceptable acid addition salt thereof.

10. The method of claim 1 wherein the compound used is 4-amino-5-chloro-2-methoxy-N-(1-isopropyl-2-methyl-4-pyrazolidinyl)benzamide or a pharmaceutically acceptable acid addition salt thereof.

11. The method of claim 1 wherein the compound used is 4-amino-5-chloro-2-methoxy-N-(1-benzyl-2-methyl-4-pyrazolidinyl)benzamide or a pharmaceutically acceptable acid addition salt thereof.

12. The method of claim 1 wherein the compound used is 4-amino-5-chloro-2-methoxy-N-(1-cyclohexyl-2-methyl-4-pyrazolidinyl)benzamide or a pharmaceutically acceptable acid addition salt thereof.

13. The method of claim 1 wherein the compound used is 4-amino-5-chloro-2-methoxy-N-[1,2-bis(1-methylethyl)-4-pyrazolidinyl]benzamide or a pharmaceutically acceptable acid addition salt thereof.

14. The method of claim 1 wherein the compound used is 4-amino-5-chloro-N-(1-ethyl-4,5-dihydro-1H-pyrazol-4-yl)-2-methoxybenzamide.

15. The method of claim 1 wherein the compound used is 4-amino-5-chloro-N-(4,5-dihydro-1-methyl-1H-pyrazol-4-yl)-2-methoxybenzamide.

16. The method of claim 1 wherein the compound used is 5-bromo-N-(1,2-diethyl-4-pyrazolidinyl)-2,4-dimethoxybenzamide or a pharmaceutically acceptable acid addition salt thereof.

17. The method of claim 1 wherein the compound used is 4-amino-5-chloro-2-methoxy-N-(4,5-dihydro-1-methyl-1H-pyrazol-4-yl)benzamide.

18. The method of claim 1 wherein the compound used is N-(1,2-diethyl-4-pyrazolidinyl)-2-methoxy-5-(methylsulfonyl)benzamide or a pharmaceutically acceptable acid addition salt thereof.

19. The method of claim 1 wherein the compound used is N-(1,2-diethyl-4-pyrazolidinyl)-2-methoxybenzamide or a pharmaceutically acceptable acid addition salt thereof.

20. The method of claim 1 wherein the compound used is 5-chloro-N-(1,2-diethyl-4-pyrazolidinyl)-2-methoxy-4-(methylamino)benzamide or a pharmaceutically acceptable acid addition salt thereof.

21. The method of claim 1 wherein the compound used is N-(1,2-diethyl-4-pyrazolidinyl)-2,4-dimethoxybenzamide or a pharmaceutically acceptable acid addition salt thereof.

22. A method of enhancing learning or memory in living animals which comprises administering thereto an effective amount of a compound selected from the group having the formula:

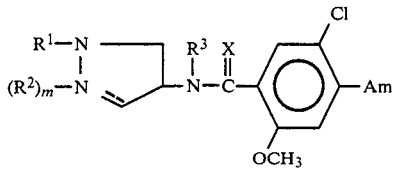
wherein:
R[1] and R[2] are selected from hydrogen, loweralkyl, phenyl, or phenylloweralkyl;
m is zero or one and when m is zero, the dotted line represents a double bond;
R[3] is hydrogen or loweralkyl;
X is oxygen or sulfur;
Am is amino (i.e., $-NH_2$) or loweralkylamino; the active optical isomers; and the pharmaceutically acceptable acid addition salts thereof.
* * * * *